US011455810B2

(12) United States Patent
Edwards et al.

(10) Patent No.: US 11,455,810 B2
(45) Date of Patent: Sep. 27, 2022

(54) DRIVER ATTENTION STATE ESTIMATION

(71) Applicant: SEEING MACHINES LIMITED, Australian Capital Territory (AU)

(72) Inventors: Timothy James Henry Edwards, Victoria (AU); John Noble, Australian Capital Territory (AU)

(73) Assignee: SEEING MACHINES LIMITED, Australian Capital Territory (AU)

( * ) Notice: Subject to any disclaimer, the term of this patent is extended or adjusted under 35 U.S.C. 154(b) by 0 days.

(21) Appl. No.: 17/280,591

(22) PCT Filed: Sep. 30, 2019

(86) PCT No.: PCT/AU2019/051056
§ 371 (c)(1),
(2) Date: Mar. 26, 2021

(87) PCT Pub. No.: WO2020/061650
PCT Pub. Date: Apr. 2, 2020

(65) Prior Publication Data
US 2021/0374443 A1    Dec. 2, 2021

(30) Foreign Application Priority Data
Sep. 28, 2018   (AU) .................................. 2018903678

(51) Int. Cl.
*G06V 20/59*         (2022.01)
*B60W 40/08*         (2012.01)
(Continued)

(52) U.S. Cl.
CPC ........... *G06V 20/597* (2022.01); *B60W 40/08* (2013.01); *G06F 3/013* (2013.01); *G06V 10/25* (2022.01);
(Continued)

(58) Field of Classification Search
None
See application file for complete search history.

(56) References Cited

U.S. PATENT DOCUMENTS

| 2005/0073136 A1* | 4/2005 | Larsson .................. A61B 5/11 |
| | | 180/272 |
| 2014/0139655 A1 | 5/2014 | Mimar |
| 2018/0096475 A1 | 4/2018 | Jemander et al. |

OTHER PUBLICATIONS

William A. Perez, Mary Anne Bertola, Jason F. Kennedy and John A. Molino, "Driver visual behavior in the presence of commercial electronic variable message signs (CEVMS)", Report No. FHWA-HEP-11 14, published Sep. 2012, 70 pages.
(Continued)

*Primary Examiner* — Thomas S McCormack
(74) *Attorney, Agent, or Firm* — FisherBroyles, LLP; Jason P. Mueller

(57) ABSTRACT

A disclosed system is configured to estimate an attention state of a subject within a scene. An imaging camera captures digital images of the subject and one or more light sources illuminate the subject during a period in which the digital images are captured. The system also includes a processor that processes the captured images to generate subject attention data of the subject. The processor further generates a primary visual attention ray of the subject from current subject attention data; generates a distribution of visual attention rays having an origin common to the primary visual attention ray; projects the visual attention rays onto a digital representation of the scene having a plurality of predefined regions of interest; determines an intersection of the projected visual attention rays with one or more of the regions of interest; and based on the intersection, estimates an attention state of the subject's attention.

19 Claims, 11 Drawing Sheets

(51) Int. Cl.
*G06F 3/01* (2006.01)
*G06V 10/25* (2022.01)
*G06V 10/60* (2022.01)
*G06V 40/19* (2022.01)

(52) U.S. Cl.
CPC .............. *G06V 10/60* (2022.01); *G06V 40/19* (2022.01); *B60W 2540/225* (2020.02); *B60W 2540/229* (2020.02)

(56) References Cited

OTHER PUBLICATIONS

Mikio Danno and Juha M. Kortelainen, "Detection of a driver's visual attention using the online UFOV method", 2010 13th International IEEE, Annual Conference on Intelligent Transportation Systems, Madeira Island, Portugal, Sep. 19-22, 2010, pp. 770-776.
Extended European Search Report issued in App. No. EP19864309.0, dated Jun. 3, 2022, 9 pages.

* cited by examiner

DRIVER ATTENTION STATE ESTIMATION

RELATED APPLICATIONS

This application is a national stage entry under 35 U.S.C. 371 of PCT/AU2019/051056, filed Sep. 30, 2019, which in turn claims priority to Australian Patent Application No. 2018903678, filed Sep. 28, 2018, the disclosures of which are incorporated herein by reference.

FIELD

This disclosure relates to monitoring systems and to a method and system for estimating an attention state of a subject being monitored, such as a vehicle driver. While some embodiments will be described herein with reference to that application, it will be appreciated that the disclosure is not limited to such a field of use, and is applicable in broader contexts.

BACKGROUND

Any discussion of the background throughout the specification should in no way be considered as an admission that such background information is widely known or forms part of common general knowledge in the field.

Driver monitoring systems rely on estimating driver head pose and eye gaze direction. However, for these parameters to be useful, it is necessary to accurately know the scene geometry to identify where the driver's attention is projected. Raw gaze and head pose data are quite noisy and are associated with varying degrees of uncertainty. This uncertainty leads to errors in the estimation of a driver's attention state.

The inventor has identified a desire to more accurately or efficiently estimate an attention state of a vehicle driver or other subject being monitored.

SUMMARY

In accordance with a first aspect of the disclosure there is provided a method of estimating an attention state of a subject within a scene using a monitoring system, the monitoring system including an imaging camera to capture images of the subject and generate subject attention data of the subject, the system configured to perform operations including:
a) generating a primary visual attention ray of the subject from current subject attention data;
b) generating an angular distribution of visual attention rays having an origin common to the primary visual attention ray;
c) projecting the primary visual attention ray and the angular distribution of visual attention rays onto a digital representation of the scene having a plurality of predefined regions of interest to thereby generate projected visual attention rays;
d) determining an intersection of the projected visual attention rays with one or more of the regions of interest; and
e) based on the intersection, determining an estimated attention state of the subject's attention.

In some embodiments, the subject attention data includes one or both of eye gaze and head pose data.

In some embodiments, the method includes the initial stage of determining an availability of current subject attention data. If current eye gaze data is available, the primary visual attention ray is generated based on the current eye gaze data. If current eye gaze data is not available, the primary visual attention ray is generated based on current head pose data.

In some embodiments, the method includes the stage of determining a confidence measure of visual attention. In some embodiments, the angular distribution of visual attention rays is distributed based, at least in part, on the confidence measure. In some embodiments, the confidence measure is based on the angle of the primary visual attention ray relative to a position and/or orientation of the imaging camera.

In some embodiments, stage e) includes determining a number of intersections of the projected visual attention rays with the one or more regions of interest. The estimated attention state may include a likely region of interest of the subject's attention. In some embodiments, the likely region of interest of the subject's attention is designated as the region of interest which has the most intersecting visual attention rays.

In some embodiments, stage e) further includes applying a weighting to particular regions of interest. The weighting may be applied dynamically. The weighting may be based on recent subject attention behavior. Thus, in some embodiments, the likely region of interest of the subject's attention is determined as the region of interest having the highest value based on a weighted sum of intersections of the visual attention rays with the one or more regions of interest. The weighting may be applied based on the size of the region of interest.

The estimated attention state may include a designation that the subject's attention is outside the one or more regions of interest.

In some embodiments, the distribution of visual attention rays is a gaussian distribution. In some embodiments, the distribution has a standard deviation based on a customary ocular motor range of a human. In some embodiments, the distribution has a standard deviation based on a real-time estimate of the confidence measure. The confidence measure may include an RMS error of the visual attention ray.

In accordance with a second aspect of the disclosure there is provided a monitoring system configured to perform a method according to the first aspect.

In accordance with a third aspect of the disclosure there is provided a system for estimating an attention state of a subject within a scene, the system including:
an imaging camera to capture digital images of the subject;
one or more light sources configured to illuminate the subject during a period in which the digital images are captured; and
a processor configured to:
  process the captured images and generate subject attention data of the subject;
  generate a primary visual attention ray of the subject from current subject attention data;
  generate an angular distribution of visual attention rays having an origin common to the primary visual attention ray;
  project the visual attention rays onto a digital representation of the scene having a plurality of predefined regions of interest;
  determine an intersection of the projected visual attention rays with one or more of the regions of interest; and
  based on the intersection, estimate an attention state of the subject's attention.

In some embodiments, the subject attention data includes one or both of eye gaze and head pose data.

In some embodiments, the processor is further configured to determine a confidence measure of visual attention. In some embodiments, the angular distribution of visual attention rays is distributed based, at least in part, on the confidence measure. In some embodiments, the confidence measure is based on the angle of the primary visual attention ray relative to a position and/or orientation of the imaging camera.

BRIEF DESCRIPTION OF THE DRAWINGS

Disclosed embodiments are described, by way of example only, with reference to the accompanying drawings in which.

DETAILED DESCRIPTION

This disclosure is described herein with reference to a driver monitoring system for monitoring a driver of a vehicle such as a car, truck or mining vehicle. However, it will be appreciated that disclosed embodiments are also applicable to monitoring the attention of subjects in other scenarios such as piloting aircraft, watercraft, trains and flight simulators.

System Overview

Figure 1:
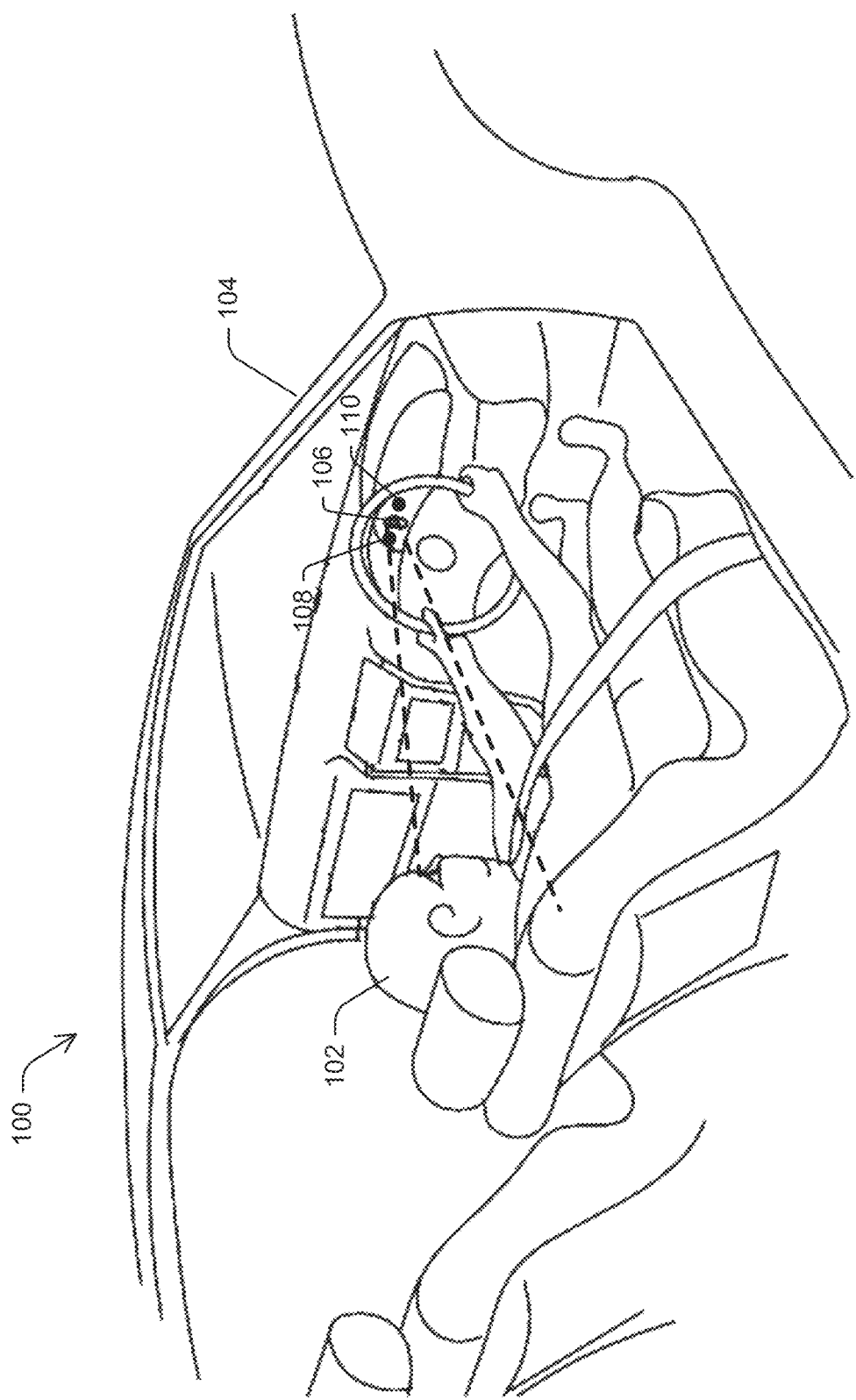
FIG. 1 is a perspective view of the interior of a vehicle having a driver monitoring system including a camera and two LED light sources installed therein.
Figure 2:
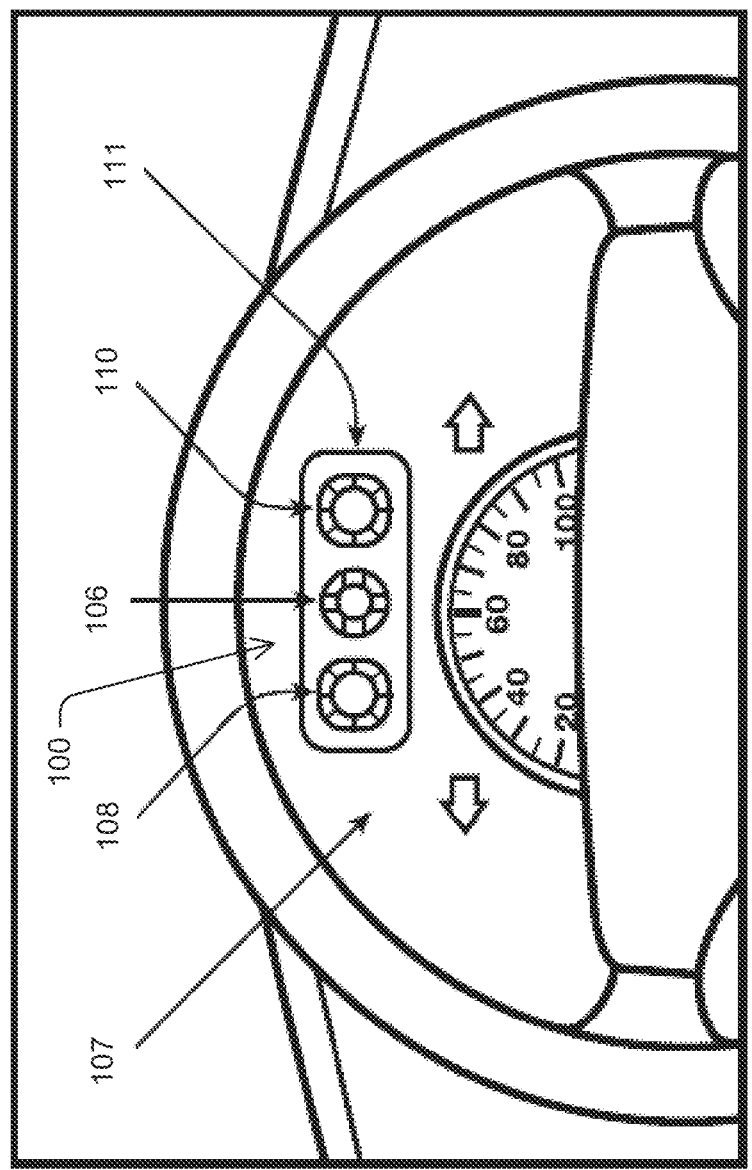
FIG. 2 is an illustration of a driver's perspective view of an automobile dashboard having the driver monitoring system of FIG. 1 installed therein.
Figure 3:
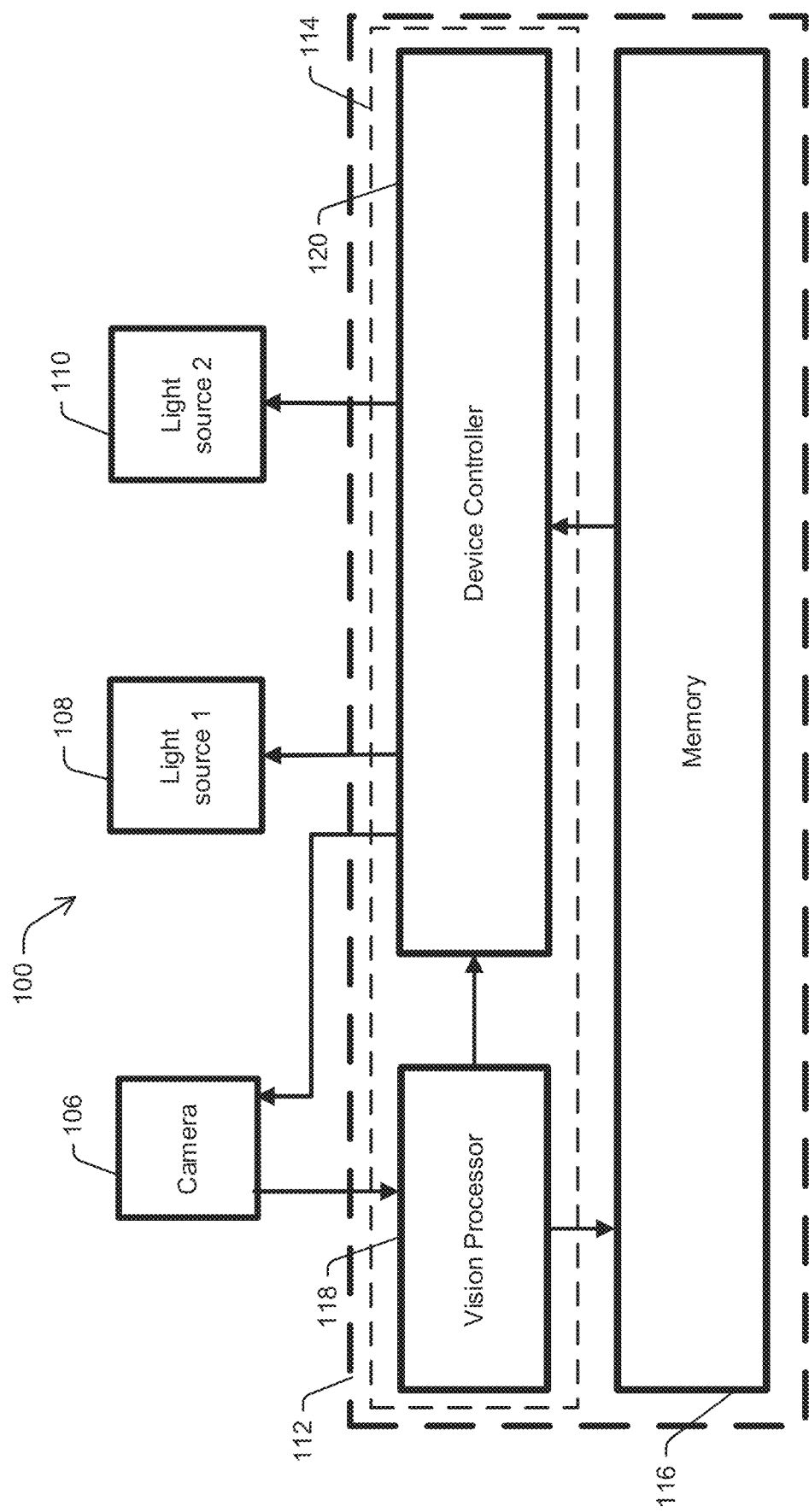
FIG. 3 is a schematic functional view of a driver monitoring system according to FIGS. 1 and 2.

Referring initially to FIGS. 1 to 3, there is illustrated a driver monitoring system 100 for capturing images of a vehicle driver 102 during operation of a vehicle 104. System 100 is further configured to perform various image processing algorithms on the captured images such as facial detection, facial feature detection, facial recognition, facial feature recognition, facial tracking or facial feature tracking, such as tracking a person's eyes. Example image processing routines are described in U.S. Pat. No. 7,043,056 to Edwards et al. entitled "Facial Image Processing System" and assigned to Seeing Machines Pty Ltd (hereinafter "Edwards et al."), the contents of which are incorporated herein by way of cross-reference.

As best illustrated in FIG. 2, system 100 includes an imaging camera 106 that is positioned on or in the vehicle dash 107 instrument display and oriented to capture images of the driver's face in the infrared wavelength range to identify, locate and track one or more human facial features.

Camera 106 may be a conventional CCD or CMOS based digital camera having a two-dimensional array of photosensitive pixels and optionally the capability to determine range or depth (such as through one or more phase detect elements). The photosensitive pixels are capable of sensing electromagnetic radiation in the infrared range. Camera 106 may also be a three-dimensional camera such as a time-of-flight camera or other scanning or range-based camera capable of imaging a scene in three dimensions. In other embodiments, camera 106 may be replaced by a pair of like cameras operating in a stereo configuration and calibrated to extract depth. Although camera 106 is may be configured to image in the infrared wavelength range, it will be appreciated that, in alternative embodiments, camera 106 may image in the visible range.

Referring still to FIG. 2, system 100 also includes a pair of infrared light sources in the form of light emitting diodes (LEDs) 108 and 110, horizontally symmetrically disposed at respective positions proximate to camera 106 on vehicle dash 107. LEDs 108 and 110 are configured to illuminate driver 102 with infrared radiation during a time when camera 106 is capturing an image, so as to enhance the driver's face to obtain high quality images of the driver's face or facial features. Operation of camera 106 and LEDs 108 and 110 in the infrared range reduces visual distraction to the driver. LEDs 108, 110 may be operated continuously, intermittently or periodically and may be operated alternatively in a strobed fashion which provides operational advantages in reducing glare present in the images. Operation of camera 106 and LEDs 108, 110 is controlled by an associated controller 112 which includes a computer processor or microprocessor and memory for storing and buffering the captured images from camera 201. In other embodiments, different types of light sources may be used in place of LEDs.

As best illustrated in FIG. 2, camera 106 and LEDs 108 and 110 may be manufactured or built as a single unit 111 having a common housing. The unit 111 is shown installed in a vehicle dash 107 and may be fitted during manufacture of the vehicle or installed subsequently as an after-market product. In other embodiments, the driver monitoring system 100 may include one or more cameras and light sources mounted in any location suitable to capture images of the head or facial features of a driver, subject and/or passenger in a vehicle. By way of example, cameras and LEDs may be located on a steering column, rearview mirror, center console or driver's side A-pillar of the vehicle. Also, in some embodiments, more than two light sources may be employed in the system. In the illustrated embodiment, the first and a second light source each include a single LED. In other embodiments, each light source may each include a plurality of individual LEDs arranged in a spatial configuration.

In the illustrated embodiment, LEDs 108 and 110 may be spaced apart horizontally by a distance in the range of about 2 cm to 10 cm and located about 30 cm to 80 cm from the driver's face. The separation of LEDs 108 and 110 is variable provided that the LEDs are located sufficiently off-axis from the camera such that red-eye effects are not present in the captured images. By way of example, red-eye effects (or "bright pupil" conditions) can typically be avoided when the LEDs illuminate the driver at angles greater than about 3 degrees from the camera optical axis when operating at 980 nm wavelengths.

More generally, avoiding red-eye effects is more complex than a simple illumination angle. Some embodiments of the disclosure are configured to avoid red-eye effects and operate in "dark pupil" conditions. Such conditions not only require the light sources to be located greater than a predetermined angle from the camera, as viewed from the driver along an optical axis, but are also influenced by many other factors including:

the dilation (size) of the pupil;
the gaze angle relative to the camera;
the age and ethnicity of the subject; and
the wavelength of light.

In dark pupil conditions, the red-eye effects are removed or substantially reduced and specular reflections on glasses do not overlap enough to degrade tracking. Driver monitoring systems operating in dark pupil conditions can provide enhanced performance in terms of higher eyelid and gaze availability and accuracy. In some embodiments, system 100 is configured to operate when only one or a subset of the LEDs are positioned in a dark pupil condition.

Turning now to FIG. 3, the functional components of system 100 are illustrated schematically. A system controller 112 acts as the central processor for system 100 and is configured to perform a number of functions as described below. Controller 112 is located within the dash 107 of vehicle 104 and may be coupled to or integral with the vehicle on-board computer. In another embodiment, controller 112 may be located within a housing together with camera 106 and LEDs 108 and 110. The housing is able to be sold as an after-market product, mounted to a vehicle dash and subsequently calibrated for use in that vehicle. One example after-market driver monitoring system available is the Guardian™ system developed by Seeing Machines Limited. In further embodiments, such as flight simulators, controller 112 may be an external computer or device such as a personal computer.

Controller 112 may be implemented as any form of computer processing device or portion of a device that processes electronic data, e.g., from registers and/or memory to transform that electronic data into other electronic data that, e.g., may be stored in registers and/or memory. As illustrated in FIG. 3, controller 112 includes a microprocessor 114, executing code stored in memory 116, such as random access memory (RAM), read-only memory (ROM), electrically erasable programmable read-only memory (EE-PROM), and other equivalent memory or storage systems as should be readily apparent to those skilled in the art.

Microprocessor 114 of controller 112 includes a vision processor 118 and a device controller 120. Vision processor 118 and device controller 120 represent functional elements which are both performed by microprocessor 114. However, it will be appreciated that, in alternative embodiments, vision processor 118 and device controller 120 may be realized as separate hardware such as microprocessors in conjunction with custom or specialized circuitry (e.g. Field Programmable Gate Arrays).

Vision processor 118 is configured to process the captured images to perform the driver monitoring based on subject attention data. For example, the subject attention data may include a three-dimensional head pose and/or eye gaze position/direction of the driver 102 within the monitoring environment. To achieve this, vision processor 118 utilizes one or more eye gaze determination algorithms. This may include, by way of example, the methodology described in Edwards et al.

Although not illustrated, system 100 may also include a forward-facing camera such as a dash-mounted, rearview mirror-mounted or front grille-mounted camera positioned to image a forward road scene. This forward-facing camera or cameras may be integrated with system 100 so that the camera is controlled by controller 120 and captured images of the forward road scene may be processed by vision processor 118.

One output of driver monitoring algorithms performed by vision processor 118 is a unified gaze ray. This ray represents the direction of current attention of driver 102 and may be represented as a three-dimensional element vector indicating an origin in three-dimensional space and a three-dimensional direction unit vector indicating a direction in the three-dimensional space. The unified gaze ray may be formed from subject attention data including but not limited to eye gaze data and/or head pose data depending on the availability of data during current image frames. By way of example, if eye gaze data of both of the driver's eyes can be obtained (both eyes visible and open), then the unified gaze ray may have an origin at the midpoint between the two eye centers. If one eye is not visible, then the unified gaze ray may have its origin at the one visible eye. If neither eye is visible, then the unified gaze ray may be determined by a head pose direction and centered on a region of the driver's head.

Vision processor 118 may also perform various other functions including determining attributes of the driver 5 such as eye closure, blink rate and tracking the driver's head motion to detect sleepiness or other issues that may interfere with the driver safely operating the vehicle. These various other identified attributes may also form the subject attention data.

The raw image data, gaze position data and other data obtained by vision processor 118 is stored in memory 116.

Device controller 120 is configured to control various parameters of camera 106 such as a shutter speed image sensor exposure/integration time, and to selectively actuate LEDs 108 and 110 in a sequenced manner in sync with the exposure/integration time of camera 106. For example, LED 108 may be controlled to activate during odd image frames and LED 110 is controlled to active during even image frames to perform a strobing sequence. Other illumination sequences may be performed by device controller 120, such as L,L,R,R,L,L,R,R . . . or L,R,0,L,R,0,L,R,0 . . . where "L" represents left mounted LED 108, "R" represents right mounted LED 110 and "0" represents an image frame captured while both LEDs are deactivated. LEDs 108 and 110 may be electrically coupled to device controller 120 but may also be controlled wirelessly by controller 120 through wireless communication such as Bluetooth™ or WiFi™ communication.

Thus, during operation of vehicle 104, device controller 120 activates camera 106 to capture images of the face of driver 102 in a video sequence. LEDs 108 and 110 are activated and deactivated in synchronization with consecutive image frames captured by camera 106 to illuminate the driver during image capture. Working in conjunction, device controller 120 and vision processor 118 provide for capturing and processing images of the driver to obtain driver state information such as drowsiness, driver attention, and head and eye gaze position during an ordinary operation of vehicle 104.

Additional components of the system may also be included within the common housing of unit 111 or may be provided as separate components according to other additional embodiments. In one embodiment, the operation of controller 112 is performed by an onboard vehicle computer system which is coupled to camera 106 and LEDs 108 and 112.

Driver Attention State Estimation

Figure 4:
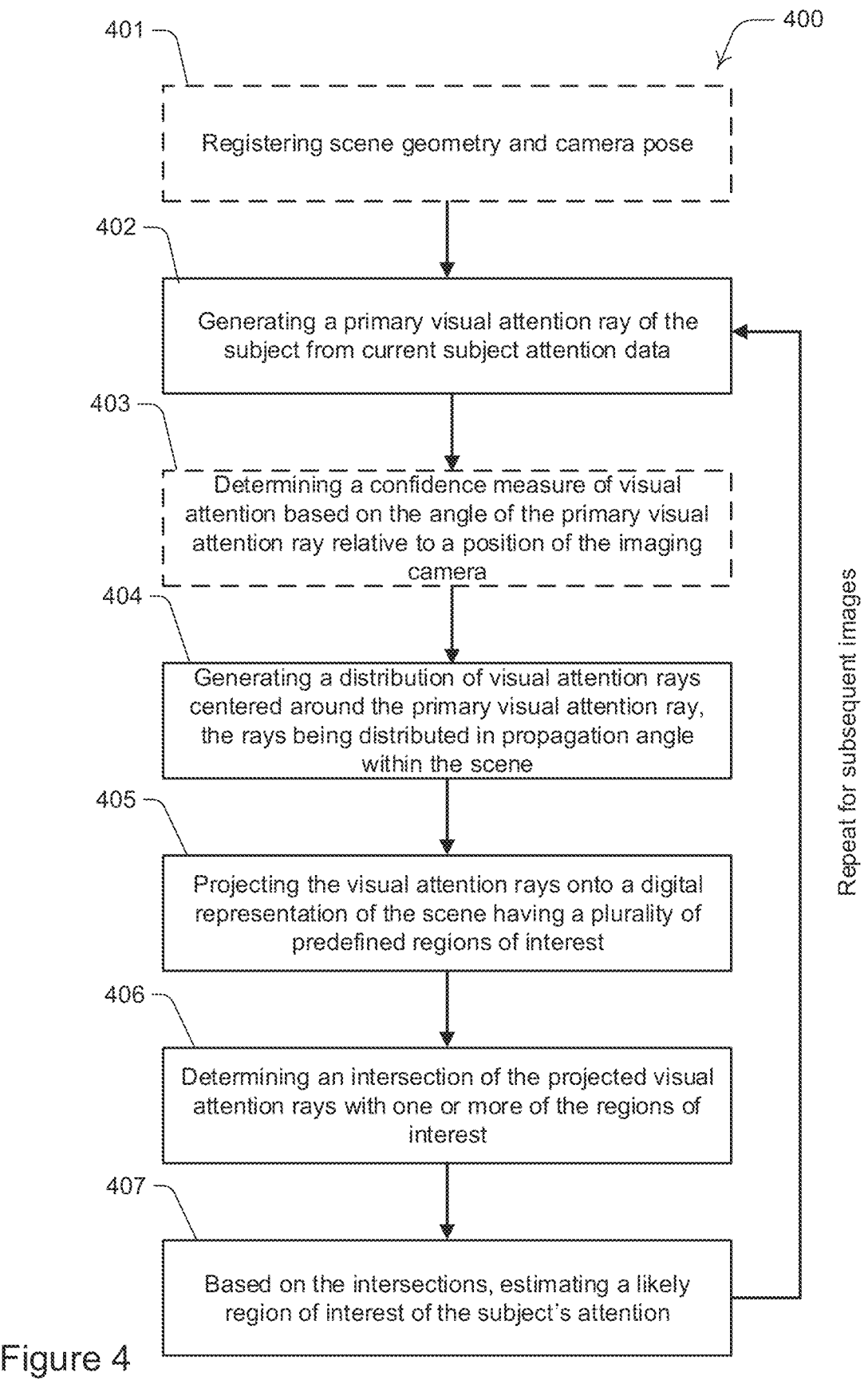
FIG. 4 is a process flow diagram illustrating the primary stages in a method of estimating an attention state of a driver.
Figure 5:
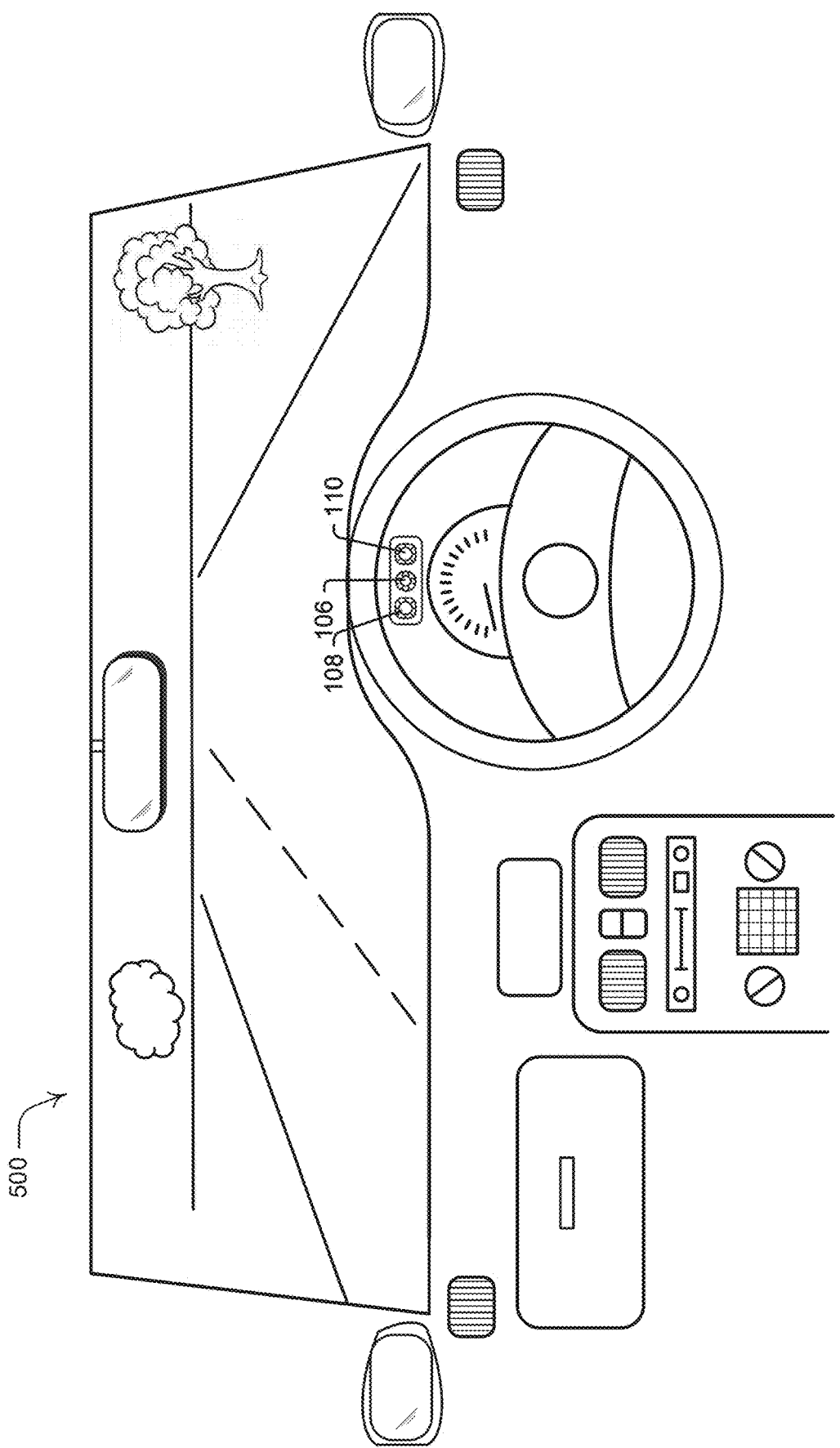
FIG. 5 is a schematic view of a driving scene as viewed from the perspective of a driver of the vehicle.

Referring now to FIG. 4, there is illustrated a method 400 of estimating an attention state of driver 102 within a driving scene using a driver monitoring system such as system 100. Method 400 is performed by vision processor 118. The driving scene may include the interior of vehicle 102, a view of the forward road scene and other regions such as the side and rearview mirrors and vehicle side road scene. An example driving scene 500 as viewed from a driver is illustrated in FIG. 5.

To perform method 400, an initial setup stage 401 is performed. At stage 401, driving scene 500 is digitally represented such that the three-dimensional geometry of objects and regions within the scene are known. The scene geometry may be determined, at least in part, from a three-dimensional model of the vehicle such as a CAD model provided by a vehicle manufacturer. The scene geometry may also be determined from one or more two or three-dimensional images of scene 500 captured by camera 106 or other cameras in or around scene 500. In either embodiment, the digital representation of scene 500 may include positions and orientations of known features within scene 500, which may be defined in a reference coordinate frame. By way of example, the known features may include individual vehicle dashboard instruments, definable cabin contours, edges, or objects or the entire vehicle cabin itself. The features may be fixed in time and space relative to a frame of reference such as a vehicle frame of reference defined relative to a region of the vehicle frame.

Example methodology on registration of scene geometry is described in PCT Patent Application Publication WO 2018/000037 A1 to Noble et al., entitled "Systems and methods for identifying pose of cameras in a scene" and assigned to Seeing Machines Limited (hereinafter "Noble et al."). The contents of Noble et al. is incorporated herein by way of cross reference. By way of example, a reference coordinate system may be defined as having a z-axis aligned along the vehicle drive shaft (longitudinal dimension), an x-axis aligned along the front wheel axle (defining a transverse dimension) with the right wheel being in the positive direction and a y-axis defining a generally vertical dimension to complete the orthogonal coordinate system.

At initial stage 401, the three-dimensional position and orientation of camera 106 (collectively representing a camera pose) is also determined in the same frame of reference as scene 500. Methodology for determining a camera pose within a scene is also described in Noble et al.

Figure 6:
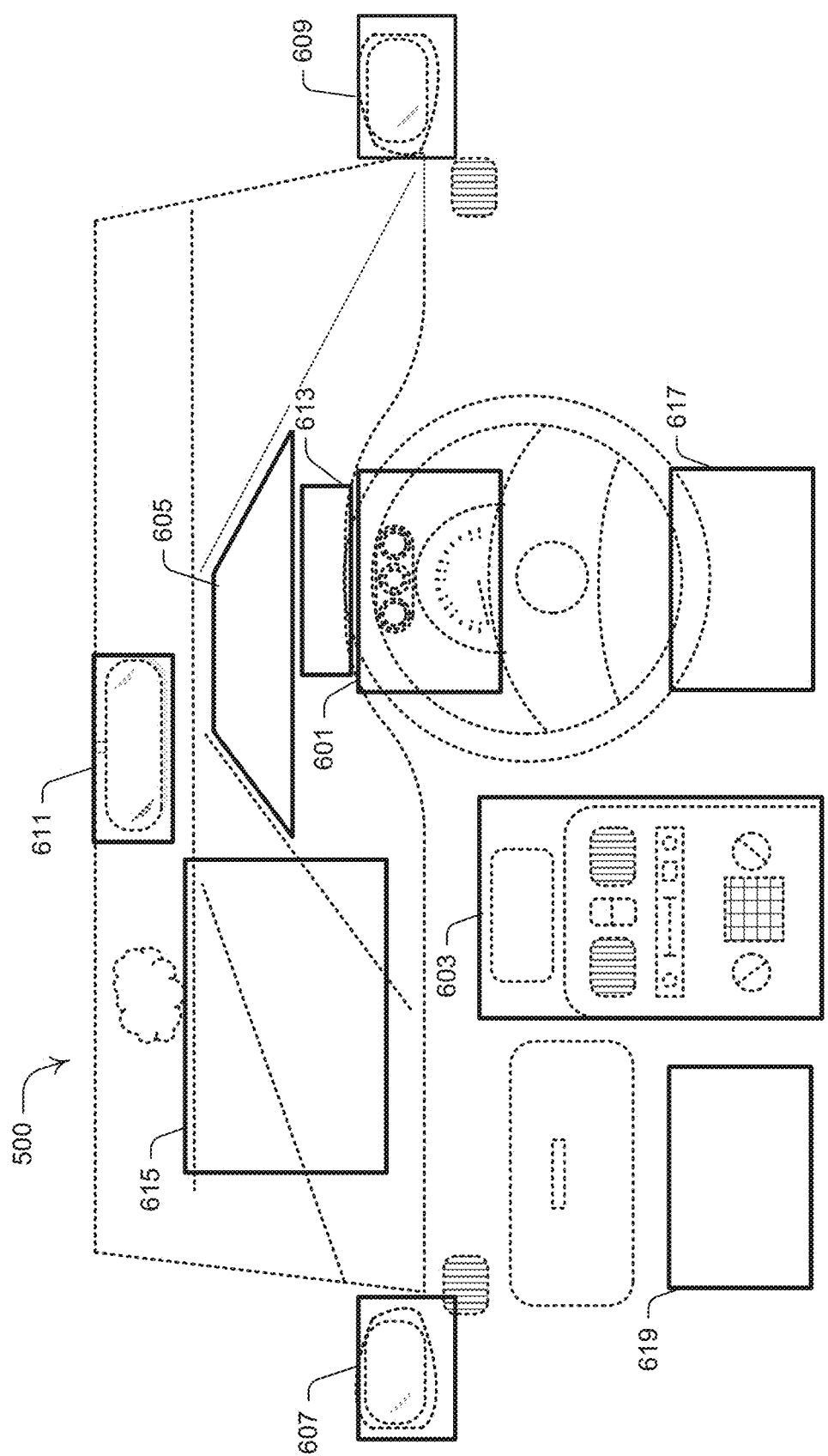
FIG. 6 is a schematic view of the driving scene of FIG. 5 illustrating regions of interest.

The scene 500 includes at least one and may include a number of regions of interest (ROIs), which are digitally designated regions within scene 500 to represent objects or areas of common viewing by driver 102. Example regions of interest are illustrated in FIG. 6 and include a vehicle instrument cluster ROI 601, center console ROI 603, center of forward road ROI 605, left side mirror ROI 607, right side mirror ROI 609, rearview mirror ROI 611, HUD display ROI 613, passenger side on road ROI 615, driver lap ROI 617 and passenger footwell ROI 619. Various other ROIs may be designated depending on the scene, vehicle model and objects contained therein.

The ROIs may be represented within scene 500 as polygonal geometry or mesh regions with appropriate dimensions specified in the coordinates of the vehicle frame of reference. Further, the ROIs may be static or dynamic. Static ROIs include fixed objects or regions within or on vehicle 104 (using a fixed vehicle frame of reference), such as the rearview mirror and side mirrors. Dynamic ROIs include objects or regions that vary dynamically in size, position and/or shape over time with respect to the vehicle frame of reference. Example dynamic regions include the forward road scene and objects viewed by the driver through the front or side windows, or through the rearview mirror.

Figure 7:
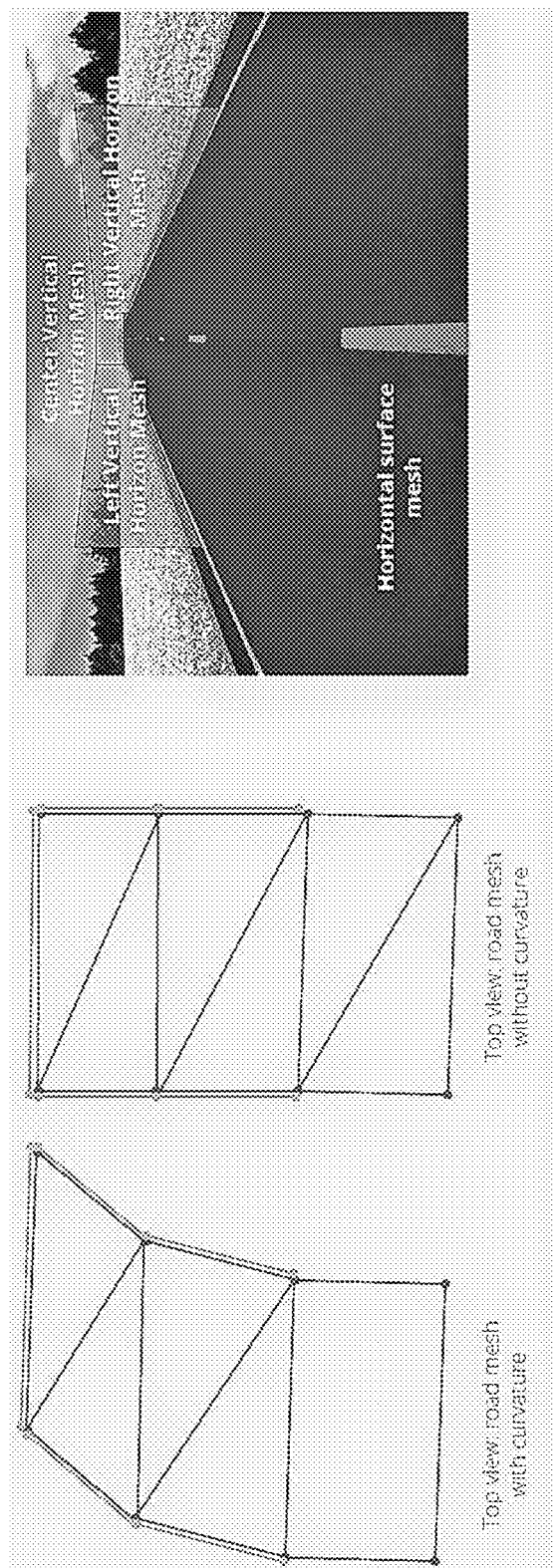
FIG. 7 is a schematic illustration of a dynamic mesh representation of a forward road region and corresponding regions of interest round that road region.

By way of example, the road scene ROI 605 may be defined by a unique, dynamic mesh item that represents the road ahead. This is illustrated schematically in FIG. 7. The geometry of the mesh is deformed during processing based on per-frame input from a forward-facing camera (e.g. dash-mounted camera) which parameterizes a current road situation. This is done in terms of properties like curvature, gradient, lane count, etc. As illustrated in FIG. 7, the road mesh may include the horizontal road surface itself, and also vertical planes capturing the central horizon above the road where driving-related activity occurs.

Returning to FIG. 4, stage 401 is illustrated as a dashed box as it represents an initial configuration stage which is not performed during a primary loop. Although, stage 401 may be performed at predetermined intervals to recalibrate the scene geometry.

Using the system operation described above, camera 106 is configured to capture images of driver 102 and generate driver attention data. The generation of driver attention data may include determining one or both of eye gaze data and/or head pose data of driver 102, which is determined from driver monitoring algorithms such as that described in Edwards et al. However, it will be appreciated that the driver attention data may include other measures. Method 400 is performed by vision processor 118 in real-time or near real-time.

At stage 402, vision processor 118 generates a primary visual attention ray of driver 102 from current subject attention data. As mentioned above, the primary visual attention ray includes a direction vector component projected from an origin representing a point on driver 102 that represents a current direction of driver attention. In some embodiments, the primary visual attention ray may be the unified gaze ray described above. By way of example, a primary visual attention ray may be represented as having an origin of <0.7, 0.5, 1> and a direction of <1, −0.2, −0.8>.

Stage 402 includes determining an availability of current visual attention data for performing subsequent stages. This includes interrogating vision processor 118 and/or memory 116 to determine whether eye gaze data is available for a current image frame or for recent image frames within a predetermined time period. Where current eye gaze data is available, the primary visual attention ray may be generated as a unified gaze ray based on the current eye gaze data. Where current eye gaze data is not available, the primary visual attention ray may be generated based on current head pose data.

At optional stage 403, a confidence measure of visual attention is determined for the primary visual attention ray. This confidence may be specified as a rational number between 0 and 1 or other arbitrary range and may be based on one or more definable factors calculated by vision processor 118 from the captured images. Example factors used to determine the confidence measure include:

- A visibility of the driver's eyes (for eye gaze) or other facial features such as nostrils, eye lids and mouth corners (for head pose). This may include the presence or absence of sunglasses.
- A degree of eye closure. This may be calculated for one or both eyes and be determined as a number within a predefined range (e.g. between 0 and 1),
- Presence of reflections and glare in the current images being processed. These may be quantified through brightness and contrast measurements in the images or regions of the images.
- A position of the driver's head relative to camera 106. The confidence measure will be reduced when the driver's head is further offset from a central camera pose axis of camera 106.
- A rotation of the driver's head relative to camera 106. The confidence measure will be reduced when the driver's head is further rotated with respect to a central camera pose axis of camera 106.
- Previous driver attention behavior. If driver 102 is detected as performing a predictable head movement, the confidence may be improved in the direction of movement.

The determination of a confidence measure is optional in that the subsequent stages may be performed without this stage.

The confidence measure may be defined based on an RMS error or deviation of the visual attention ray. It is possible to obtain a real-time or near real-time validation of the RMS error from data using glints (specular corneal reflections) identified in the captured images. One method of determining glints in images is described in PCT Patent Application Publication WO 2015/027289 A1 to Rougeaux, entitled "Method and apparatus for eye detection from glints" and assigned to Seeing Machines Limited.

At stage 404, a distribution of visual attention rays is generated. Like the primary visual attention ray, the individual rays of the distribution of visual attention rays are specified as a three-dimensional position vector representing origin and a three-dimensional direction vector representing direction. The distributed rays have the same three-dimensional origin as the primary visual attention ray.

The distribution is centered around the primary visual attention ray generated in stage 402 and the rays are distributed in direction within the scene according to a predefined distribution function. By way of example, the distribution of angles of visual attention rays may be a normal or Gaussian distribution. It will be appreciated that various other types of distributions may be implemented here, and the choice to do so is within the skill of the person skilled in the art.

The distribution may be defined such that the primary visual attention ray forms the mean or expected value of the distribution. Where the visual attention data includes eye gaze data, the standard deviation of the distribution may be based on the confidence measure determined in stage 403 such that a higher confidence measure results in a smaller standard deviation and therefore smaller spread of angles of gaze rays. In one embodiment, the standard deviation is equal to the confidence measure determined in stage 403. Where the visual attention data includes head pose, the standard deviation of the distribution may be based on a customary ocular motor range of a human. This is a measure of the typical maximum deviation between head pose relative to eye gaze direction in humans. By way of example, the customary ocular motor range may be about 20°±10°.

The distribution of visual attention rays may be generated by applying a Monte Carlo type method constrained to a normal or gaussian probability distribution to produce a predefined number of statistical outcomes.

Figure 8A:
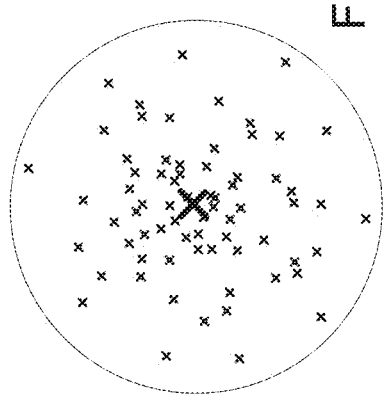
FIG. 8A illustrates a side view of a two-dimensional distribution of visual attention ray positions, as distributed according to a normal distribution around a primary visual attention ray displayed in bold.
Figure 8B:
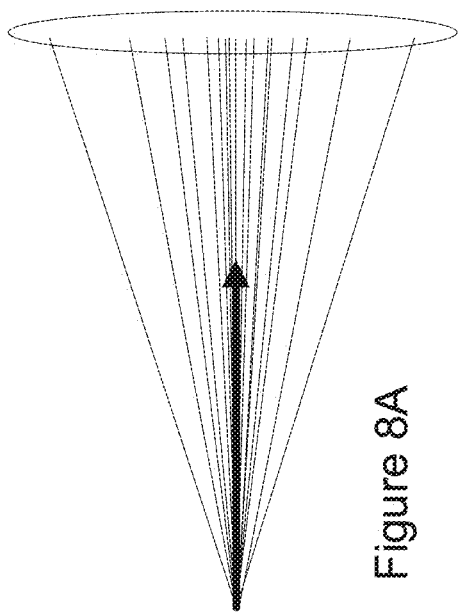
FIG. 8B illustrates a cross section view of the distribution of FIG. 8A, with the primary visual attention ray represented as an 'X'.
Figure 8C:
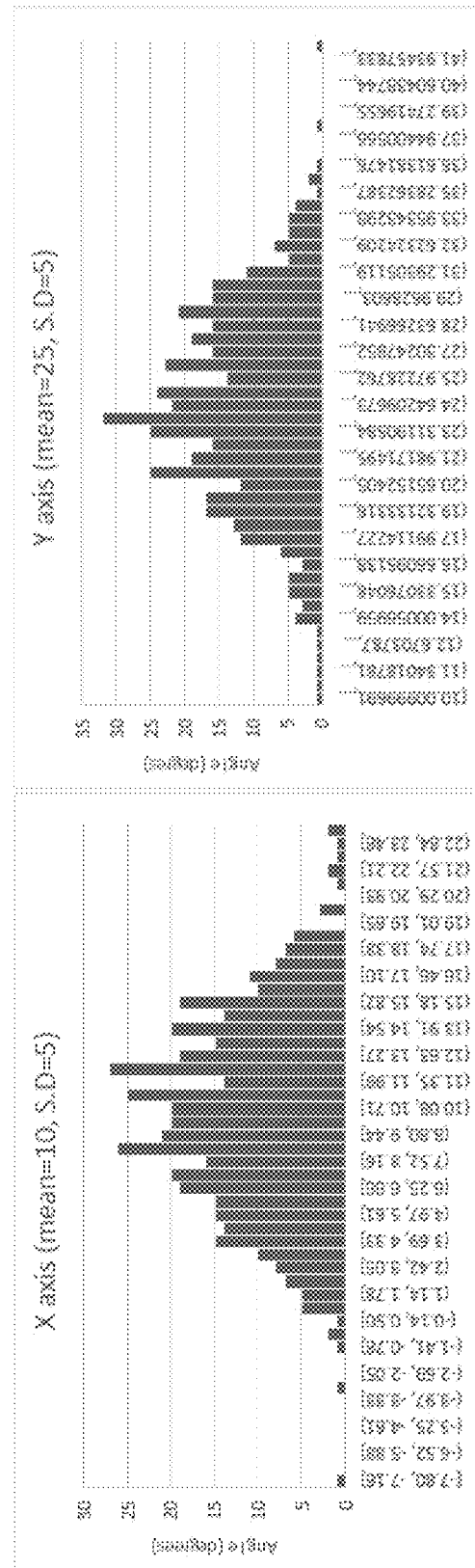
FIG. 8C illustrates graphs for x and y axes (representing angle) for 450 visual attention rays distributed according to a normal distribution having a mean x, y angle of (10°, 25°) and a standard deviation of 5°.

An example normal distribution of visual attention rays is illustrated in FIG. 8A-C. FIG. 8A illustrates a side view of the distribution, with the primary visual attention ray displayed in bold. FIG. 8B illustrates a resulting two-dimensional distribution of visual attention ray positions, as distributed according to a normal distribution around the primary visual attention ray (shown in bold). FIG. 8C illustrates graphs for x and y axes (representing angle) for 450 sample visual attention rays distributed according to a normal distribution having a mean x, y angle of (10°, 25°) and a standard deviation of 5°. It will be appreciated that, in a three-dimensional scene, the angles are represented as three dimensional vectors.

In some circumstances, the distribution of visual attention rays may not be equally constrained in the different dimensions. For example, the driver's past behavior may be monitored from the attention state of past images and this may have a bearing on how the distribution of visual attention rays are defined. This may be taken into account in determining the confidence or when generating the distribution (through appropriate constraints).

Figure 9:
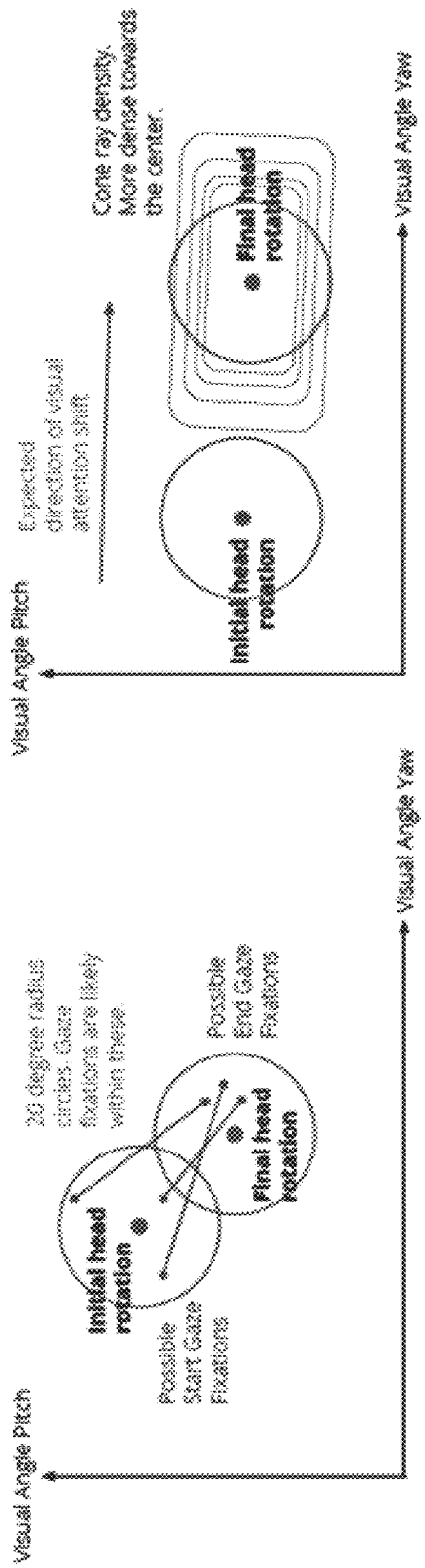
FIG. 9 illustrates a constraint of distribution in visual attention rays during a head movement of a driver.

By way of example, and with reference to FIG. 9, driver 102 may be performing a head movement from left to right over a series of past images. Head direction tends to lag gaze direction by varying amounts up to a maximum. For example, it is uncomfortable for a human to rotate their eyes 60° away from where their head is pointing. Deviations over 20° are uncommon. As a result, the direction of head rotation change is expected to match the direction of visual attention change. The exact gaze angles for the initial and final gaze fixation are unknown, (using only head rotation as a predictor), but the direction can be inferred with some confidence.

In this exemplary circumstance, the distribution or rays within a head direction cone (defined by the confidence) is concentrated in the direction of head rotation change, as shown schematically in the right panel of FIG. 9. Here the compressed vertical dimensions of the ray distribution box represents an increased confidence level.

Figure 10:
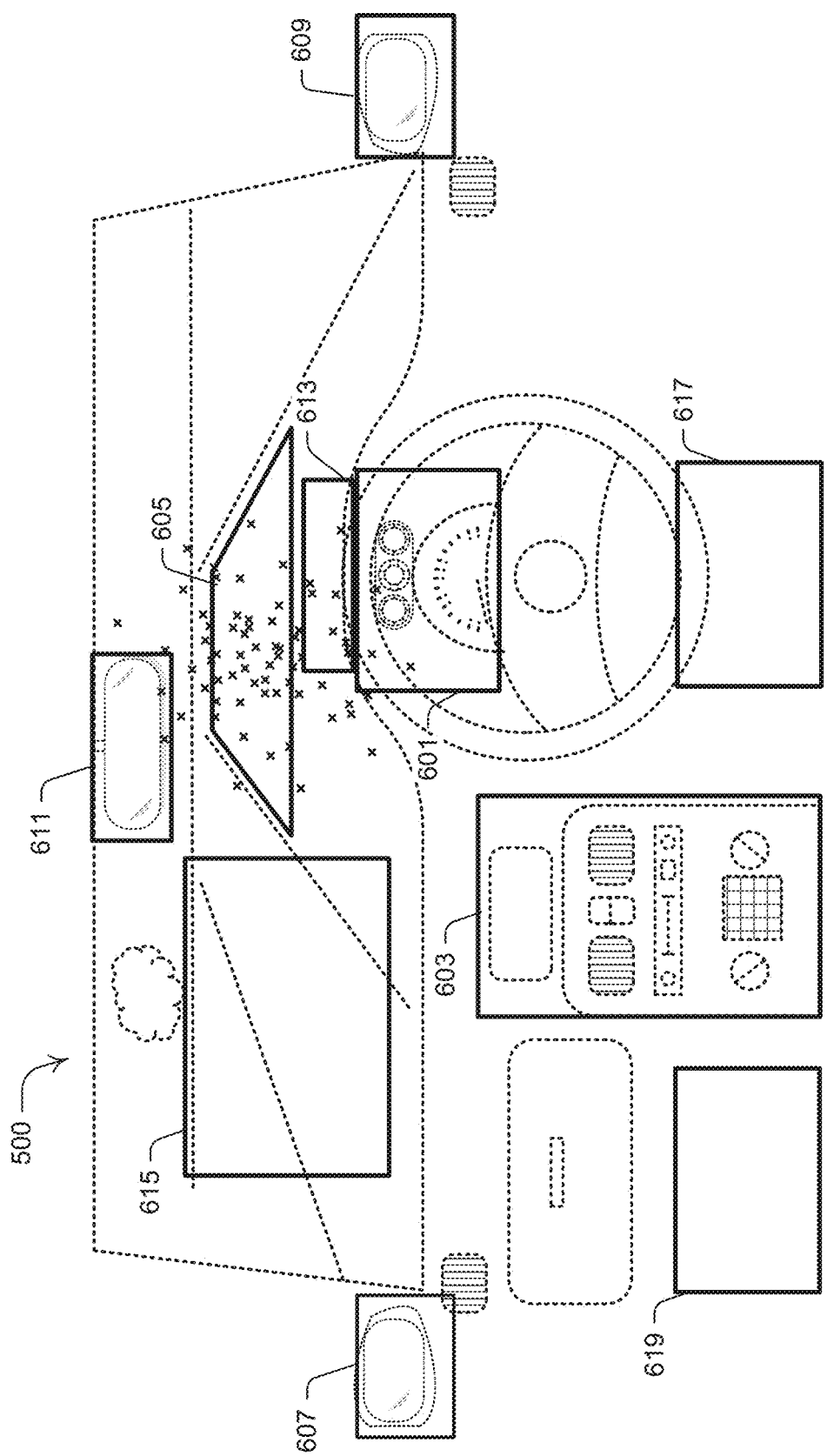
FIG. 10 illustrates a projection of intersection points of visual attention rays onto a driving scene.

At stage, 405, the distributed visual attention rays are projected onto the digital representation of scene 500, which has a plurality of predefined regions of interest. FIG. 10 illustrates an exemplary projection of intersection points of visual attention rays onto scene 500. This projection is achieved by determining which points in the three-dimensional digital representation of scene 500 the visual attention rays intersect. The rays originate at the point of origin defined by the primary visual attention ray (e.g. unified gaze ray from the driver) and project along their vector trajectories at their distributed angles through scene 500.

At stage 406, an intersection of the projected visual attention rays with one or more of the regions of interest is determined. In FIG. 10, the projected visual attention rays intersect with ROIs 601, 605, 611 and 613, with the remainder intersecting with regions outside the ROIs. This determination includes performing a comparison of the projected coordinates or angles of each ray with the predefined coordinates of the ROIs within the digital scene.

Based on the intersections determined in stage 406, at stage 407, an attention state of driver 102 is estimated. Depending on the intersections, the estimated attention state may include a likely region of interest of the subject's attention or may include a designation that the driver's attention is outside the ROIs. In this latter case, the driver's attention may be designated as being "off-road", "unidentified" or the like. These designations of attention state are described below.

The estimation of an attention state may involve a number of calculations, such as determining a number of intersections of the projected visual attention rays with the various ROIs. The estimation may also involve applying a weighting to particular regions of interest which may be applied dynamically. For example, the weighting may be based on recent subject attention behavior. In general, drivers tend to perform predetermined behavioral patterns in driving a vehicle. For example, the driver behavior patterns may be learned by a machine learning process or through driver behavior input from a human factors expert. By learning these behavioral patterns, current driver attention can be used to predict future driver attention patterns and, as a consequence, weight predicted ROIs more heavily.

By way of example, drivers typically glance between the instrument cluster (represented by ROI 601) and forward road (represented by ROI 605) intermittently. Thus, if a glance towards the instrument cluster is detected in previous images, it can be predicted that a glance back to the forward road will follow shortly. Thus, ROI 605 corresponding to the forward road may be weighted more heavily than other ROIs such as the rearview mirror ROI 611. In this circumstance, the estimated ROI of the driver's attention may be designated as ROI 605 even if more visual attention rays fall within ROI 611. The weighting may be a number between 0 and 1 or may be a number within another arbitrary but predefined range. Weighting may also be applied to smaller ROIs as less visual attention rays are likely to intersect smaller regions.

Thus, in some embodiments, the likely ROI of the driver's attention may simply be designated as the ROI which has the most intersecting visual attention rays. However, in other embodiments, the likely ROI of the driver's attention may be determined as the ROI having the highest value based on a weighted sum of intersections of the visual attention rays with the regions of interest.

Using the above method, a driver monitoring system (or other monitoring system) is able to estimate an attention state of the driver as a function of time. Method 400 may be performed on a frame-by-frame basis. Alternatively, to reduce computational complexity at the cost of temporal resolution, method 400 may be performed only on a subset of processed images. By way of example, if images are captured at 60 Hz, method 400 may be performed on every 10 images to provide an attention state estimation at a rate of 6 Hz.

Exemplary Implementation

Figure 11:
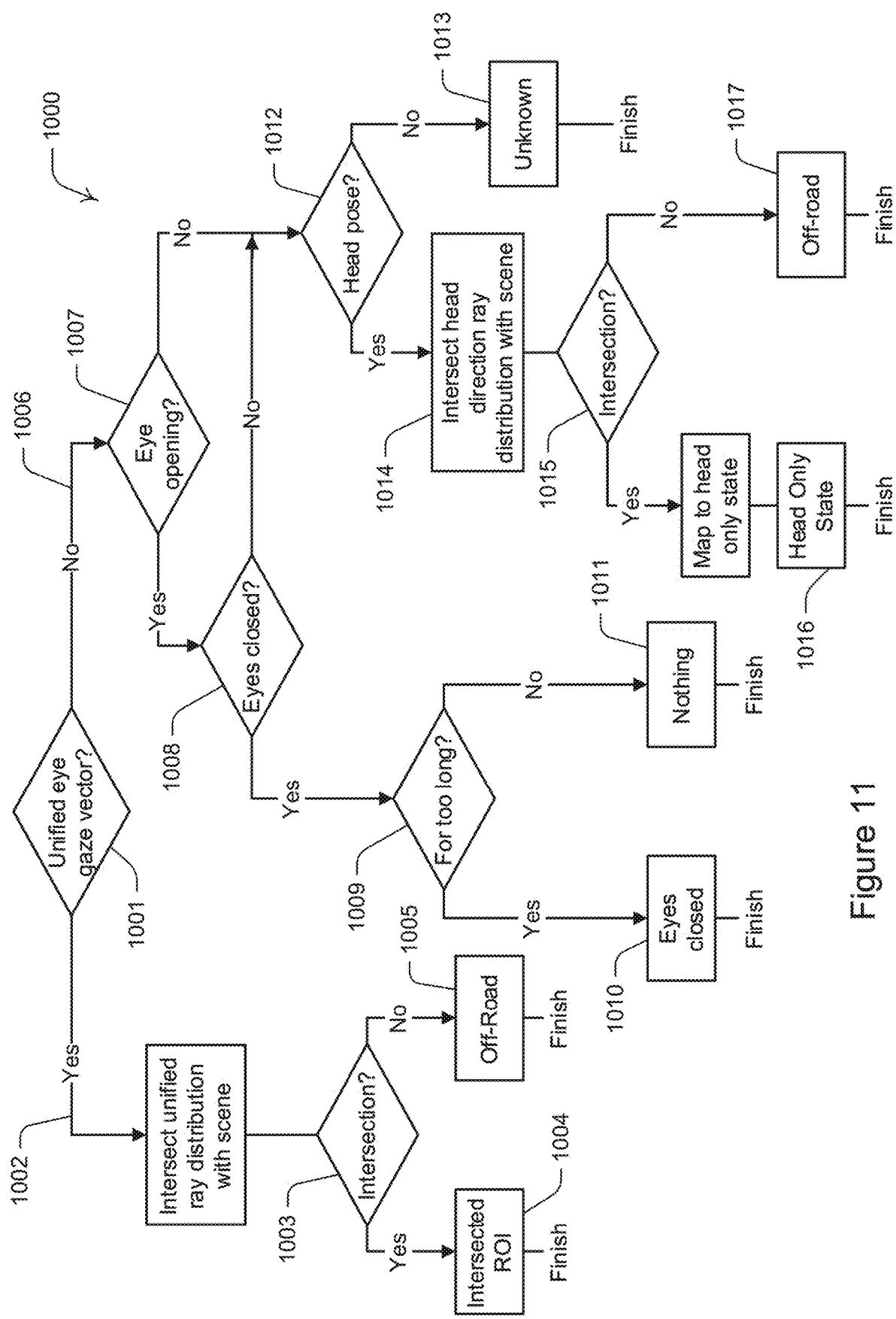
FIG. 11 illustrates a decision tree of the flow of control in an exemplary implementation of a method of estimating an attention state of a driver.

Method 400 may include various other decisions throughout the process of estimating an attention state. An example decision tree 1000, for an implementation of method 400 by vision processor 118 is illustrated in FIG. 11. At block 1001, a determination is made as to whether a unified eye gaze ray from eye gaze data can be determined from a current image being processed. If a unified eye gaze ray can be determined (if one or both eyes are visible and open), then control follows path 1002 and method 400 is performed with the unified eye gaze ray as the primary attention ray. At block 1003, the visual attention state is designated as either a likely intersected ROI at block 1004, or as "off-road" at block 1005. The designation of "off-road" represents a default where the likely attention state falls outside all designated ROIs.

If, at block 1001, a unified eye gaze ray cannot be determined, control follows path 1006. At block 1007, a determination of possible eye opening is performed on the current image. If one or both eyes are sufficiently distinguishable so as to permit a determination of eye opening, control moves to block 1008, where a determination is made as to whether or not the eye or eyes are closed. Methods for determination of a closure state include U.S. Pat. No. 5,878,156 entitled "Detection of The Open/closed State of Eyes Based on Analysis of Relation Between Eye and Eyebrow Images in Input Face Images". This document describes a technique for detecting the open/closed state of the eyes based on analysis of relation between eye and eyebrow images in input face images. Further, Edwards et al. teaches a method of determining eye closure based on detection of eye corners, eyelid edges, fitting curves to the eyelids and calculating eye closure degree.

If the eye or eyes are determined to be closed at block 1008, then control moves to block 1009, in which a determination is made as to whether the eyes have been closed for too long. Block 1009 relies on determinations of eye closure from earlier images and a comparison with a predefined threshold time (e.g. 1 second). If the eyes are determined to have been closed for too long, then, at block 1010, the driver attention state is designated as "eyes closed" and an appropriate action may be taken (such as to issue an alert to the driver). If the eyes are determined to have only been closed momentarily (less than the predefined threshold), such as during a blink, then, at block 1011, the driver attention state is either not estimated or designated as "nothing" or the like for that image frame. This reflects the fact that visual attention is not directed at anything in the environment around the driver for this particular image frame.

If, at block 1008, the eye or eyes are determined to be opened, or the eye opening cannot be determined at block 1007, then control moves to block 1012. Here, a determination of head pose is made. If head pose is not able to be determined at block 1012, then, at block 1013, the current driver attention state is designated as being "unknown" for this image frame. If, the head pose is able to be determined at block 1012, then control shifts to block 1014 where method 400 is performed with the primary visual attention ray determined by the head pose of driver 102. Finally, at block 1015, the visual attention state is designated as either a likely intersected ROI at block 1016 or as "off-road" at block 1017 where the likely attention state falls outside all designated ROIs. In the case of using head pose data, every ROI has a head-only fallback state. The head-only states are a fixed set, with less granularity than what is achievable with gaze results.

After the driver attention state has been estimated, method 400, including the process flow illustrated in decision tree 1000, is performed on a subsequent image in the captured image sequence.

CONCLUSIONS

The above described system and method provides for dynamically estimating an attention state of a vehicle driver or subject in another monitoring scenario. The data generated is useful for real-time or near real-time driver monitoring and also for longer term statistical studies of driver behavior and analytics.

INTERPRETATION

Throughout this specification, use of the term "element" is intended to mean either a single unitary component or a collection of components that combine to perform a specific function or purpose.

Unless specifically stated otherwise, as apparent from the following discussions, it is appreciated that throughout the specification discussions utilizing terms such as "processing," "computing," "calculating," "determining", "analyzing" or the like, refer to the action and/or processes of a computer or computing system, or similar electronic computing device, that manipulate and/or transform data represented as physical, such as electronic, quantities into other data similarly represented as physical quantities.

In a similar manner, the term "controller" or "processor" may refer to any device or portion of a device that processes electronic data, e.g., from registers and/or memory to transform that electronic data into other electronic data that, e.g., may be stored in registers and/or memory. A "computer" or a "computing machine" or a "computing platform" may include one or more processors.

Reference throughout this specification to "one embodiment", "some embodiments" or "an embodiment" means that a particular feature, structure or characteristic described in connection with the embodiment is included in at least one embodiment of the disclosure. Thus, appearances of the phrases "in one embodiment", "in some embodiments" or "in an embodiment" in various places throughout this specification are not necessarily all referring to the same embodiment. Furthermore, the particular features, structures or characteristics may be combined in any suitable manner, as would be apparent to one of ordinary skill in the art from this disclosure, in one or more embodiments.

As used herein, unless otherwise specified the use of the ordinal adjectives "first", "second", "third", etc., to describe a common object, merely indicate that different instances of like objects are being referred to, and are not intended to imply that the objects so described must be in a given sequence, either temporally, spatially, in ranking, or in any other manner.

In the claims below and the description herein, any one of the terms "comprising", "comprised of" or "which comprises" are open terms that mean including at least the elements/features that follow, but not excluding others. Thus, the term "comprising", when used in the claims, should not be interpreted as being limitative elements or stages listed thereafter. For example, the scope of the expression "a device comprising A and B" should not be limited to devices consisting only of elements A and B. Any one of the terms "including" or "which includes" or "that includes" as used herein is also an open term that also means including at least the elements/features that follow the term, but not excluding others. Thus, "including" is synonymous with and means "comprising".

It should be appreciated that in the above description of exemplary embodiments of the disclosure, various features of the disclosure are sometimes grouped together in a single embodiment, Fig., or description thereof for the purpose of streamlining the disclosure and aiding in the understanding of one or more embodiments. This method of disclosure, however, is not to be interpreted as reflecting an intention that the claims require more features than are expressly recited in each claim. The claims following the Detailed Description are hereby expressly incorporated into this Detailed Description, with each claim standing on its own as a separate embodiment of this disclosure.

Furthermore, while some embodiments described herein include some but not other features included in other embodiments, combinations of features of different embodiments are meant to be within the scope of the disclosure, and form different embodiments, as would be understood by those skilled in the art. For example, in the following claims, any of the claimed embodiments can be used in any combination.

In the description provided herein, numerous specific details are set forth. However, it is understood that embodiments of the disclosure may be practiced without these specific details. In other instances, conventional methods, structures and techniques have not been shown in detail in order not to obscure an understanding of this description.

Similarly, it is to be noticed that the term "coupled", when used in the claims, should not be interpreted as being limited to direct connections only. The terms "coupled" and "connected," along with their derivatives, may be used. It should be understood that these terms are not intended as synonyms for each other. Thus, the scope of the expression "a device A coupled to a device B" should not be limited to devices or systems wherein an output of device A is directly connected to an input of device B. It means that there exists a path between an output of A and an input of B which may be a path including other devices systems. "Coupled" may mean that two or more elements are either in direct physical, electrical or optical contact, or that two or more elements are not in direct contact with each other but yet still co-operate or interact with each other.

Thus, while example embodiments have been described, those skilled in the art will recognize that other and further modifications may be made thereto without departing from the spirit of the disclosure, and it is intended to claim all such changes and modifications as fall within the scope of the disclosure. For example, any formulas given above are merely representative of procedures that may be used. Functionality may be added or deleted from the block diagrams and operations may be interchanged among functional blocks. Stages may be added or deleted to methods described within the scope of the present disclosure.

We claim:

1. A method of estimating an attention state of a subject within a scene using a monitoring system, the monitoring system including an imaging camera configured to capture images of the subject and a processor circuit configured to generate subject attention data of the subject, the method comprising:
   a) generating a primary visual attention ray of the subject from current subject attention data, the primary visual attention ray including an origin and a direction;
   b) generating an angular distribution of visual attention rays having an origin common to the primary visual attention ray;
   c) projecting the primary visual attention ray and the angular distribution of visual attention rays onto a digital representation of the scene having a plurality of predefined regions of interest to thereby generate projected visual attention rays;
   d) determining intersections of the projected visual attention rays with one or more of the regions of interest;
   e) applying weightings to particular regions of interest; and
   f) based on the intersections, determining an estimated attention state of the subject's attention including a likely region of interest of the subject's attention; and
   wherein the likely region of interest of the subject's attention is determined as the region of interest having the either the most intersecting visual attention rays or the highest value based on a weighted sum of intersections of the visual attention rays with the one or more regions of interest.

2. The method according to claim 1, wherein the subject attention data includes one or both of eye gaze and head pose data.

3. The method according to claim 2, further comprising: determining an availability of current subject attention data.

4. The method according to claim 3, wherein, when current eye gaze data is available, the primary visual attention ray is generated based on the current eye gaze data and, when current eye gaze data is not available, the primary visual attention ray is generated based on current head pose data.

5. The method according to claim 1, further comprising: determining a confidence or error measure of visual attention.

6. The method according to claim 5, wherein the angular distribution of visual attention rays is distributed based, at least in part, on the confidence or error measure.

7. The method according to claim 6, wherein the confidence or error measure is based on an angle of the primary visual attention ray relative to a position and/or orientation of the imaging camera.

8. The method according to claim 1, wherein stage f) includes determining a number of intersections of the projected visual attention rays with the one or more regions of interest.

9. The method according to claim 1, wherein the weighting is based on recent subject attention behavior.

10. The method according to claim 1, wherein the likely region of interest of the subject's attention is determined as a region of interest having a highest value based on a weighted sum of intersections of the visual attention rays with the one or more regions of interest.

11. The method according to claim 1, wherein the weighting is applied based on a size of the region of interest.

12. The method according to claim 1, wherein the estimated attention state includes a designation that the subject's attention is outside the one or more regions of interest.

13. The method according to claim 1, wherein the angular distribution of visual attention rays is a gaussian distribution.

14. The method according to claim 1, wherein the angular distribution has a standard deviation based on a customary ocular motor range of a human.

15. A system for estimating an attention state of a subject within a scene, the system comprising:
   an imaging camera configured to capture digital images of the subject;
   one or more light sources configured to illuminate the subject during a period in which the digital images are captured; and
   a processor circuit configured to:
      process the captured images and to generate subject attention data of the subject;
      generate a primary visual attention ray of the subject from current subject attention data;
      generate an angular distribution of visual attention rays having an origin common to the primary visual attention ray;
      project the primary visual attention ray and the angular distribution of visual attention rays onto a digital representation of the scene having a plurality of predefined regions of interest to thereby generate projected visual attention rays;
      determine intersections of the projected visual attention rays with one or more of the regions of interest;
      applying weightings to particular regions of interest; and
   based on the intersections, determining an estimated attention state of the subject's attention including a likely region of interest of the subject's attention; and
      wherein the likely region of interest of the subject's attention is determined as the region of interest having the either the most intersecting visual attention rays or the highest value based on a weighted sum of intersections of the visual attention rays with the one or more regions of interest.

16. The method according to claim 6 wherein the distribution of visual attention rays is constrained in one or more dimensions based on the confidence or error measure.

17. The method according to claim 16 wherein the distribution of visual attention rays is constrained based on the subject's past behavior.

18. The method according to claim 16 wherein the distribution of visual attention rays is constrained based on head movement.

19. The method according to claim 6 wherein the confidence or error measure is based on one or more of a visibility of the subject's eyes or facial features, a degree of eye closure or a rotation of the subject's head relative to the imaging camera.

* * * * *